United States Patent
Kotanko et al.

(10) Patent No.: US 11,744,930 B2
(45) Date of Patent: Sep. 5, 2023

(54) INTRADIALYTIC MONITORING OF HEMODYNAMIC STATUS BASED ON DETECTION OF OXYGEN SIGNATURE PHASE SHIFT

(71) Applicant: Fresenius Medical Care Holdings, Inc., Waltham, MA (US)

(72) Inventors: Peter Kotanko, New York, NY (US); Stephan Thijssen, New York, NY (US); Priscila Preciado, New York, NY (US); Israel D. Campos, New York, NY (US); Xia Tao, New York, NY (US)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 634 days.

(21) Appl. No.: 16/841,529

(22) Filed: Apr. 6, 2020

(65) Prior Publication Data
US 2021/0308354 A1    Oct. 7, 2021

(51) Int. Cl.
*A61M 1/36*     (2006.01)
*A61M 39/02*    (2006.01)

(52) U.S. Cl.
CPC ........ *A61M 1/3607* (2014.02); *A61M 1/3661* (2014.02); *A61M 39/0247* (2013.01);
(Continued)

(58) Field of Classification Search
CPC . A61B 5/14557; A61B 5/1459; A61B 5/4848; A61B 5/6866; A61M 1/3607;
(Continued)

(56) References Cited

U.S. PATENT DOCUMENTS 5,456,253 A * 10/1995 Steuer .................. A61M 1/361
600/366
6,061,590 A    5/2000 Krivitski
(Continued)

FOREIGN PATENT DOCUMENTS

| EP | 1 236 435 A1 | 9/2002 |
| WO | WO 94/027495 A1 | 12/1994 |
| WO | WO 2004/000114 A1 | 12/2003 |

OTHER PUBLICATIONS

International Patent Application No. PCT/US2021/024741, International Search Report (dated Jul. 12, 2021).

*Primary Examiner* — Benjamin J Klein
(74) *Attorney, Agent, or Firm* — Leydig, Voit & Mayer, Ltd.

(57) ABSTRACT

A hemodialysis system includes: a hemodialysis machine configured to provide hemodialysis treatment to a patient, wherein the hemodialysis treatment includes circulating extracorporeal blood of the patient through an extracorporeal blood circuit; a first oxygen saturation sensor device configured to measure oxygen saturation corresponding to the extracorporeal blood of the patient in the extracorporeal blood circuit; a second oxygen saturation sensor device configured to measure oxygen saturation corresponding to blood flowing within the patient; and at least one controller configured to determine one or more oxygen saturation phase shift (OSPS) values or one or more transcutaneous travel time values corresponding to the patient based on oxygen saturation measurements from the first oxygen saturation sensor device and the second oxygen saturation sensor device.

21 Claims, 6 Drawing Sheets

(52) U.S. Cl.
CPC .. *A61M 2039/0276* (2013.01); *A61M 2205/18* (2013.01); *A61M 2205/3344* (2013.01); *A61M 2205/3561* (2013.01); *A61M 2210/083* (2013.01); *A61M 2230/205* (2013.01)

(58) Field of Classification Search
CPC .............. A61M 1/3609; A61M 1/3655; A61M 1/3661; A61M 39/0247; A61M 2039/0276; A61M 2205/18; A61M 2205/3344; A61M 2205/3561; A61M 2205/52; A61M 2210/083; A61M 2210/205
See application file for complete search history.

(56) References Cited

U.S. PATENT DOCUMENTS

| | | |
|---|---|---|
| 9,801,993 B2 | 10/2017 | Barrett et al. |
| 2002/0068015 A1 | 6/2002 | Polaschegg et al. |
| 2006/0149144 A1 | 7/2006 | Lynn et al. |
| 2010/0076281 A1* | 3/2010 | Navon ............... A61B 5/14552 600/323 |
| 2012/0078069 A1 | 3/2012 | Melker |
| 2012/0154789 A1* | 6/2012 | Barrett ..................... F16B 2/22 356/41 |
| 2017/0340293 A1 | 11/2017 | Al-Ali et al. |

* cited by examiner

INTRADIALYTIC MONITORING OF HEMODYNAMIC STATUS BASED ON DETECTION OF OXYGEN SIGNATURE PHASE SHIFT

BACKGROUND

Patients with kidney failure or partial kidney failure typically undergo dialysis treatment in order to remove toxins and excess fluids from their blood. Hemodialysis is one of the common forms of dialysis treatment. To perform hemodialysis, blood is taken from a patient through an intake needle or catheter which draws blood from an arteriovenous vascular access or vein, respectively, located in a specifically accepted access location—for example, a shunt surgically placed in an arm, or a central-venous catheter placed in the superior vena cava. The needle or catheter is connected to extracorporeal tubing that is fed to a peristaltic pump and then to a dialyzer that cleans the blood and removes excess fluid. The cleaned blood is then returned to the patient through additional extracorporeal tubing typically connected to another needle in the arteriovenous vascular access or to a separate lumen of the central-venous catheter. Sometimes, a heparin drip is located in the hemodialysis loop to prevent the blood from coagulating.

As the drawn blood passes through the dialyzer, it travels in straw-like tubes within the dialyzer that serve as semi-permeable passageways for the unclean blood. Fresh dialysate solution enters the dialyzer at its downstream end. The dialysate surrounds the straw-like tubes and flows through the dialyzer in the opposite direction of the blood flowing through the tubes. Fresh dialysate collects toxins passing through the straw-like tubes by diffusion and excess fluids in the blood by ultra filtration. Dialysate containing the removed toxins and excess fluids is disposed of as waste. The red cells remain in the straw-like tubes and do not pass into the dialysate.

An optical blood monitoring system is often used during hemodialysis treatment or other treatments involving extracorporeal blood flow. The optical blood monitoring system may use optical techniques to non-invasively measure in real-time the hematocrit and the oxygen saturation level of blood flowing through the hemodialysis system. The blood monitoring system may measure the blood at, for example, a sterile blood chamber attached in-line to the extracorporeal tubing.

In general, blood chambers along with the tube set and dialyzer are replaced for each patient. The blood chamber is intended for a single use. The blood chamber defines an internal blood flow cavity comprising a substantially flat viewing region and two opposing viewing lenses. Emitters (such as light-emitting diode (LED) emitters) and photodetectors for the optical blood monitoring system are fastened (e.g., by clipping) into place onto the blood chamber over the lenses. Multiple wavelengths of light may be resolved through the blood chamber and the patient's blood flowing through the chamber with a photodetector detecting the resulting intensity of each wavelength.

The preferred wavelengths to measure hematocrit are about 810 nm, which is substantially isobestic for red blood cells, and about 1300 nm, which is substantially isobestic for water. A ratiometric technique may be used to calculate the patient's hematocrit value in real-time based on this light intensity information. The hematocrit value is a percentage determined by the ratio between (1) the volume of the red blood cells in a given whole blood sample and (2) the overall volume of the blood sample.

In a clinical setting, the actual percentage change in blood volume occurring during hemodialysis can be determined, in real-time, from the change in the measured hematocrit. Thus, an optical blood monitoring system is able to non-invasively monitor not only the patient's hematocrit level but also the change in the patient's blood volume in real-time during a hemodialysis treatment session. The ability to monitor real-time change in blood volume helps facilitate safe, effective hemodialysis.

To monitor blood in real-time, emitters and photodetectors may be mounted on two opposing heads of a sensor clip assembly that fits over a blood chamber. For accuracy of the system, the emitters and the photodetectors may be located in a predetermined position and orientation each time the sensor clip assembly is clipped into place over the blood chamber. The predetermined position and orientation ensure that light traveling from the emitters to the photodetectors travels through the lenses of the blood chamber.

The optical blood monitoring system may be calibrated for the specific dimensions of the blood chamber and the specific position and orientation of the sensor clip assembly relative to the blood chamber. For this purpose, the sensor clip assembly may be configured to mate to the blood chamber so that the emitters and the photodetectors are at a predetermined position and orientation relative to one another and to the blood chamber.

An example of an optical blood monitoring system having a sensor clip assembly configured to measure hematocrit and oxygen saturation of extracorporeal blood flowing through a blood chamber is described in U.S. Pat. No. 9,801,993, titled "SENSOR CLIP ASSEMBLY FOR AN OPTICAL MONITORING SYSTEM," which is incorporated by reference in its entirety herein.

Cardiovascular disease is highly prevalent in hemodialysis patients, and the leading cause of death in this population. Cardiac output is a hemodynamic variable that corresponds to the perfusion of organs. With each pump stroke of the heart, oxygen rich arterial blood is ejected from the left ventricle and passes through arterial vessels to deliver oxygen bound to hemoglobin to the capillary beds of organs and tissues. The time it takes for oxygen to be delivered to organs and tissues is an indicator of cardiovascular function.

However, in existing hemodialysis systems, the cardiovascular function of a patient is typically not closely monitored. During hemodialysis treatment, a patient's blood pressure may be checked periodically (for example, every 30 minutes), but this only provides a rough and infrequent indication of cardiovascular function.

SUMMARY

In an exemplary embodiment, the present application provides an extracorporeal blood treatment system (such as a hemodialysis system), comprising: an extracorporeal blood treatment machine (such as a hemodialysis machine) configured to provide treatment (such as hemodialysis treatment) to a patient, wherein the treatment includes circulating extracorporeal blood of the patient through an extracorporeal blood circuit; a first oxygen saturation sensor device configured to measure oxygen saturation corresponding to the extracorporeal blood of the patient in the extracorporeal blood circuit; a second oxygen saturation sensor device configured to measure oxygen saturation corresponding to blood flowing within the patient; and at least one controller configured to determine one or more oxygen saturation phase shift (OSPS) values or one or more transcutaneous travel time values corresponding to the patient based on oxygen saturation measurements from the first oxygen saturation sensor device and the second oxygen saturation sensor device.

In a further exemplary embodiment, the extracorporeal blood of the patient is drawn from the patient from an access site, and wherein the second oxygen saturation sensor device is located on the patient ipsilateral to the access site.

In a further exemplary embodiment, the access site and the second oxygen saturation sensor device are both located on a same arm of the patient.

In a further exemplary embodiment, the second oxygen saturation sensor device is a pulse oximeter configured to be attached to a finger of the patient.

In a further exemplary embodiment, determining the one or more OSPS values or the one or more transcutaneous travel time values comprises comparing a first oxygen saturation trace corresponding to measurements taken by the first oxygen saturation sensor device with a second oxygen saturation trace corresponding to measurements taken by the second oxygen saturation sensor device.

In a further exemplary embodiment, the first oxygen saturation sensor device and the second oxygen saturation sensor device each have a sampling rate of at least 1 Hz.

In a further exemplary embodiment, the at least one controller is further configured to analyze the one or more determined OSPS values or the one or more determined transcutaneous travel time values, wherein the analysis includes a trend analysis which identifies an upward or downward trend in determined OSPS values or determined transcutaneous travel time values for the patient.

In a further exemplary embodiment, the at least one controller is further configured to analyze the one or more determined OSPS values or the one or more determined transcutaneous travel time values, wherein the analysis includes a reference-based analysis which identifies whether a determined OSPS value or a determined transcutaneous travel time value for the patient is above or below one or more reference OSPS values or one or more transcutaneous travel time value.

In a further exemplary embodiment, the one or more determined transcutaneous travel time values each correspond to an amount of time for blood to travel between an access site for drawing the extracorporeal blood and a location of the second oxygen saturation sensor device.

In a further exemplary embodiment, the at least one controller is further configured to analyze the one or more determined OSPS values or the one or more determined transcutaneous travel time values, and to output a result of the analysis, wherein outputting the result includes displaying the result on a display and/or transmitting the result over a communication network.

In a further exemplary embodiment, the at least one controller is further configured to analyze the one or more determined OSPS values or the one or more determined transcutaneous travel time values, and to execute a responsive operation in response to a result of the analysis, wherein the responsive operation includes modifying the hemodialysis treatment for the patient.

In a further exemplary embodiment, the modification includes: lowering an ultrafiltration rate; pausing the hemodialysis treatment; adjusting the patient position; lowering dialysate temperature; infusing saline; increasing sodium concentration in dialysate; and/or triggering a relatively higher frequency of blood pressure measurements.

In a further exemplary embodiment, the at least one controller is further configured to analyze the one or more determined OSPS values or the one or more determined transcutaneous travel time values, and to execute a responsive operation in response to a result of the analysis, wherein the responsive operation includes outputting an alarm and/or transmitting a message to a medical professional.

In another exemplary embodiment, the present application provides a method for monitoring hemodynamic status of a patient during a treatment, comprising: measuring, by a first oxygen saturation sensor device, oxygen saturation of extracorporeal blood of the patient at a location in an extracorporeal blood circuit; measuring, by a second oxygen saturation sensor device, oxygen saturation of blood within the patient at a location on the patient's body; determining, by at least one controller, one or more oxygen saturation phase shift (OSPS) values or one or more transcutaneous travel time values corresponding to the patient based on oxygen saturation measurements from the first oxygen saturation sensor device and the second oxygen saturation sensor device; analyzing, by the at least one controller, the one or more determined OSPS values or the one or more determined transcutaneous travel time values; and executing, by the at least one controller, a responsive operation in response to a result of the analysis.

In a further exemplary embodiment, the extracorporeal blood of the patient is drawn from the patient from an access site, and wherein the second oxygen saturation sensor device is located on the patient's body ipsilateral to the access site.

In a further exemplary embodiment, the one or more determined transcutaneous travel time values each correspond to an amount of time for blood to travel between the access site and the location of the second oxygen saturation sensor device.

In a further exemplary embodiment, the responsive operation includes modifying the treatment.

In yet another exemplary embodiment, the present application provides a non-transitory computer-readable medium having processor-executable instructions stored thereon for monitoring hemodynamic status of a patient during a treatment, wherein the processor-executable instructions, when executed, facilitate: measuring, by a first oxygen saturation sensor device, oxygen saturation of extracorporeal blood of the patient at a location in an extracorporeal blood circuit; measuring, by a second oxygen saturation sensor device, oxygen saturation of blood within the patient at a location on the patient's body; determining, by at least one controller, one or more oxygen saturation phase shift (OSPS) values or one or more transcutaneous travel time values corresponding to the patient based on oxygen saturation measurements from the first oxygen saturation sensor device and the second oxygen saturation sensor device; analyzing, by the at least one controller, the one or more determined OSPS values or the one or more determined transcutaneous travel time values; and executing, by the at least one controller, a responsive operation in response to a result of the analysis.

In a further exemplary embodiment, the extracorporeal blood of the patient is drawn from the patient from an access site, and wherein the second oxygen saturation sensor device is located on the patient's body ipsilateral to the access site.

In a further exemplary embodiment, the one or more determined transcutaneous travel time values each correspond to an amount of time for blood to travel between the access site and the location of the second oxygen saturation sensor device.

In a further exemplary embodiment, the responsive operation includes modifying the treatment.

DETAILED DESCRIPTION

Exemplary embodiments of the present application provide for improved intradialytic monitoring of hemodynamic status based on detection of one or more oxygen signature phase shift (OSPS) values or one or more transcutaneous travel time values for a patient. By using an extracorporeal oxygen saturation sensor device disposed in an extracorporeal blood line together with a transcutaneous oxygen saturation sensor device disposed on the patient's body (such as a pulse oximeter clipped to the patient's finger), one or more OSPS values or one or more transcutaneous travel time values for the patient is determined. The determination may be performed in real-time as oxygen saturation measurements are being made by the extracorporeal oxygen saturation sensor device and the transcutaneous oxygen saturation sensor device. Determined OSPS or transcutaneous travel time values provide information regarding the patient's hemodynamic status that may be indicative of cardiovascular function, and this information can be used to detect and respond to potential problems relating to hemodynamic changes in the patient that may occur during dialysis treatment.

Figure 1:
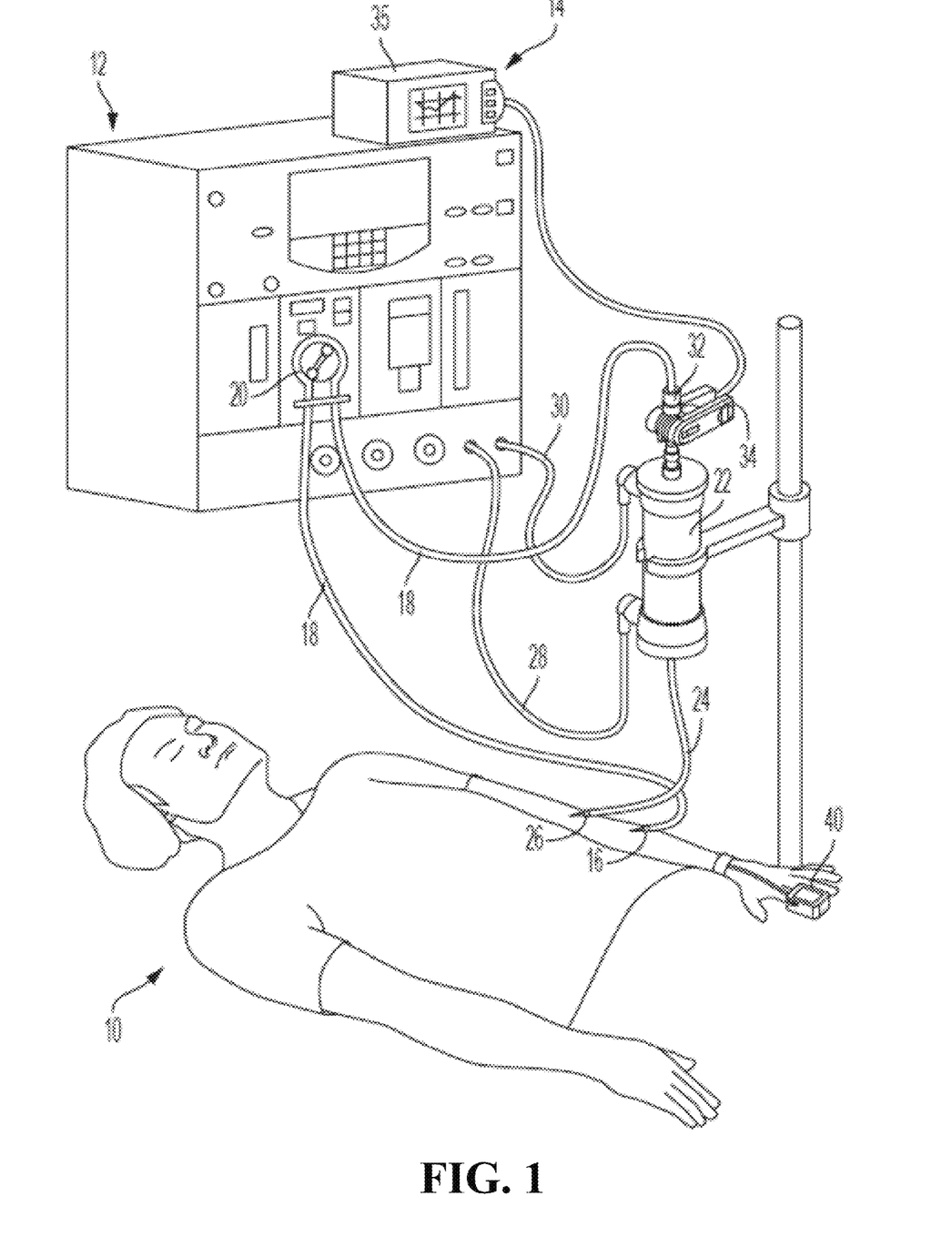
FIG. 1 is a schematic diagram of an exemplary hemodialysis system having an extracorporeal oxygen saturation sensor device and a transcutaneous oxygen saturation sensor device.

FIG. 1 is a schematic diagram of an exemplary hemodialysis system having an extracorporeal oxygen saturation sensor device and a transcutaneous oxygen saturation sensor device. In the example provided by FIG. 1, the extracorporeal oxygen saturation sensor device may be a sensor device 34 that is part of an optical blood monitoring system 14 configured for determining hematocrit, oxygen saturation, and blood volume change, and the transcutaneous oxygen saturation sensor device is a pulse oximeter 40 attached to a patient's body (e.g., clipped to the patient's finger).

In FIG. 1, a patient 10 is undergoing hemodialysis treatment using a hemodialysis machine 12. An inlet needle or catheter 16 is inserted into an access site of the patient 10 (e.g., an arterio-venous fistula or graft (AVF/AVG)), such as in the arm, and is connected to extracorporeal tubing 18 that leads to a peristaltic pump 20 and to a dialyzer 22 (or blood filter). The dialyzer 22 removes toxins and excess fluid from the patient's blood. The dialyzed blood is returned from the dialyzer 22 through extracorporeal tubing 24 and return needle or catheter 26. In some parts of the world, the extracorporeal blood flow may additionally receive a heparin drip to prevent clotting. The excess fluids and toxins are removed by clean dialysate liquid which is supplied to the dialyzer 22 via tube 28, and waste liquid is removed for disposal via tube 30. A typical hemodialysis treatment session takes about 3 to 5 hours in the United States.

The optical blood monitoring system 14 includes a display device 35 and a sensor device 34. The sensor device 34 may, for example, be a sensor clip assembly that is clipped to a blood chamber 32, wherein the blood chamber 32 is disposed in the extracorporeal blood circuit. A controller of the optical blood monitoring system 14 may be implemented in the display device 35 or in the sensor clip assembly 34, or both the display device 35 and the sensor clip assembly 34 may include a respective controller for carrying out respective operations associated with the optical blood monitoring system.

The blood chamber 32 may be disposed in line with the extracorporeal tubing 18 upstream of the dialyzer 22. Blood from the peristaltic pump 20 flows through the tubing 18 into the blood chamber 32. The sensor device 34 includes emitters that emit light at certain wavelengths and detectors for receiving the emitted light after it has passed through the blood chamber 32. For example, the emitters may include LED emitters which emit light at approximately 810 nm, which is isobestic for red blood cells, at approximately 1300 nm, which is isobestic for water, and at approximately 660 nm, which is sensitive for oxygenated hemoglobin, and the detectors may include a silicon photodetector for detecting light at the approximately 660 and 810 nm wavelengths, and an indium gallium arsenide photodetector for detecting light at the approximately 1300 nm wavelength. The blood chamber 32 includes lenses or viewing windows that allows the light to pass through the blood chamber 32 and the blood flowing therein.

A controller of the optical blood monitoring system 14 uses the light intensities measured by the detectors to determine hematocrit (HCT), oxygen saturation, and change in blood volume associated with blood passing through the blood chamber 32 to which the sensor device 34 is attached using a ratiometric model. The intensity of the received light at each of the various wavelengths is reduced by attenuation and scattering from the fixed intensity of the visible and infrared light emitted from each of the LED emitters. Beer's Law, for each wavelength of light, describes attenuation and scattering as follows:

$$i_n = I_{0-n} * e^{-\varepsilon_p X_p d_{pt}} * e^{-\varepsilon_b X_b d_b} * e^{-\varepsilon_p X_p d_{pr}} \qquad \text{Eq. (1)}$$

where $i_n$=received light intensity at wavelength n after attenuation and scattering; $I_{0-n}$=transmitted light intensity at wavelength n incident to the measured medium; e=the natural exponential term; ε=the extinction coefficient for the measured medium (p—blood chamber polycarbonate, b—blood); X=the molar concentration of the measured medium (p—blood chamber polycarbonate, b—blood); and d=the distance through the measured medium (pt—transmitting blood chamber polycarbonate, b—blood, pr—receiving blood chamber polycarbonate).

Since the properties of the polycarbonate blood chamber do not change, the first and third exponential terms in the above Eq. (1) are constants for each wavelength. Mathematically, these constant terms are multiplicative with the initial constant term $I_{0-n}$ which represents the fixed intensity of the radiation transmitted from a respective LED emitter. For simplification purposes, Eq. (1) can be rewritten in the following form using bulk extinction coefficients and a modified initial constant $I'_{0-n}$ as follows:

$$i_n = I'_{0-n} * e^{-\alpha_b d_b} \qquad \text{Eq. (2)}$$

where $i_n$=received light intensity at wavelength "n" after attenuation and scattering as though the detector were at the receive blood boundary; $\alpha$=the bulk extinction coefficient ($\alpha_b = \varepsilon_b X_b$) and $I'_{0-n}$ the equivalent transmitted light intensity at wavelength n as if applied to the transmit blood boundary accounting for losses through the blood chamber. Note that the term $I'_{0-n}$ is the light intensity incident on the blood with the blood chamber losses included.

Using the approach defined in Eq. (2) above, the 810 nm wavelength which is isobestic for red blood cells and the 1300 nm wavelength which is isobestic for water can be used to determine the patient's hematocrit. The ratio of the normalized amplitudes of the measured intensity at these two wavelengths produces the ratio of the composite extinction values $\alpha$ for the red blood cells and the water constituents in the blood chamber, respectively. A mathematical function then defines the measured HCT value:

$$HCT = f\left[\frac{\ln\left(\frac{i_{810}}{I_{0\text{-}810}}\right)}{\ln\left(\frac{i_{1300}}{I_{0\text{-}1300}}\right)}\right] \qquad \text{Eq. (3)}$$

where $i_{810}$ is the light intensity of the photo receiver at 810 nm, $i_{1300}$ is the infrared intensity of the photodetector at 1300 nm and $I_{0\text{-}810}$ and $I_{0\text{-}1300}$ are constants representing the intensity incident on the blood accounting for losses through the blood chamber. The above equation holds true assuming that the flow of blood through the blood chamber 32 is in steady state, i.e. steady pressure and steady flow rate.

The preferred function f[ ] is a second order polynomial having the following form:

$$HCT = f\left[\frac{\ln\left(\frac{i_{810}}{I_{0\text{-}810}}\right)}{\ln\left(\frac{i_{1300}}{I_{0\text{-}1300}}\right)}\right] = A\left[\frac{\ln\left(\frac{i_{810}}{I_{0\text{-}810}}\right)}{\ln\left(\frac{i_{1300}}{I_{0\text{-}1300}}\right)}\right]^2 + B\left[\frac{\ln\left(\frac{i_{810}}{I_{0\text{-}810}}\right)}{\ln\left(\frac{i_{1300}}{I_{0\text{-}1300}}\right)}\right] + C. \qquad \text{Eq. (4)}$$

A second order polynomial is normally adequate as long as the infrared radiation incident at the first and second wavelengths is substantially isobestic.

The oxygen saturation level, or the oxygenated hemoglobin level, is determined with a ratiometric model having the following form:

$$SAT = g\left[\frac{\ln\left(\frac{i_{660}}{I_{0\text{-}660}}\right)}{\ln\left(\frac{i_{810}}{I_{0\text{-}810}}\right)}\right] \qquad \text{Eq. (5)}$$

where $i_{660}$ is the light intensity of the photo receiver at 660 nm, $i_{810}$ is the intensity of the photodetector at 810 nm and $I_{0\text{-}660}$ and $I_{0\text{-}810}$ are constants representing the intensity incident on the blood accounting for losses through the blood chamber. The function g[ ] is a mathematical function determined based on experimental data to yield the oxygen saturation level, again preferably a second order polynomial. It may be useful to use a pair of second order polynomials depending on the hematocrit value or a separate 810 nm calibration for oxygen and hematocrit.

The display device 35 may be used to display determined values of hematocrit, oxygen saturation, and change in blood volume for a patient during hemodialysis treatment. Further, the display device 35 and/or the sensor device 34 may include communications hardware and/or interfaces for communicating the determined values of hematocrit, oxygen saturation, and change in blood volume to one or more other devices.

While the sensor device 34 provides oxygen saturation measurements corresponding to the patient's blood flowing through the extracorporeal circuit, the pulse oximeter 40 provides oxygen saturation measurements with respect to blood flowing through the patient's body at the location where the transcutaneous sapling is performed. In an exemplary implementation, the pulse oximeter is in communication with a controller of the optical blood monitoring system 14 (e.g., the controller of the display device 35) via a wired or wireless connection, and the controller of the optical blood monitoring system 14 utilizes the two sets of oxygen saturation measurements from the sensor device 34 and the pulse oximeter 40 to determine an OSPS or transcutaneous travel time of the patient. In an alternative implementation, another controller (such as a controller of a remote monitoring device or on a server (e.g., in a computing cloud or a local edge device of a clinic) in communication with both the optical blood monitoring system 14 and the pulse oximeter 40) may utilize the two sets of oxygen saturation measurements from the sensor device 34 and the pulse oximeter 40 to determine an OSPS or transcutaneous travel time of the patient.

The hemodialysis system depicted in FIG. 1 may be one of a plurality of hemodialysis systems in a dialysis clinic. Patients may come into the dialysis clinic for treatments at regular intervals, for example, on a Monday-Wednesday-Friday schedule or a Tuesday-Thursday-Saturday schedule.

It will be appreciated that the hemodialysis system depicted in FIG. 1 is merely exemplary. The principles discussed herein are applicable to other types of hemodialysis systems and medical systems in which at least one oxygen saturation sensor can be disposed in an extracorporeal blood line and another oxygen saturation sensor can be disposed on a patient's body. For example, the principles discussed herein may also be used in the context of other systems for providing extracorporeal therapies involving arteriovenous vascular access, such as hemodiafiltration (HDF) systems and blood treatment systems used to treat systemic inflammatory response syndrome (SIRS)/sepsis or liver failure.

Figure 2:
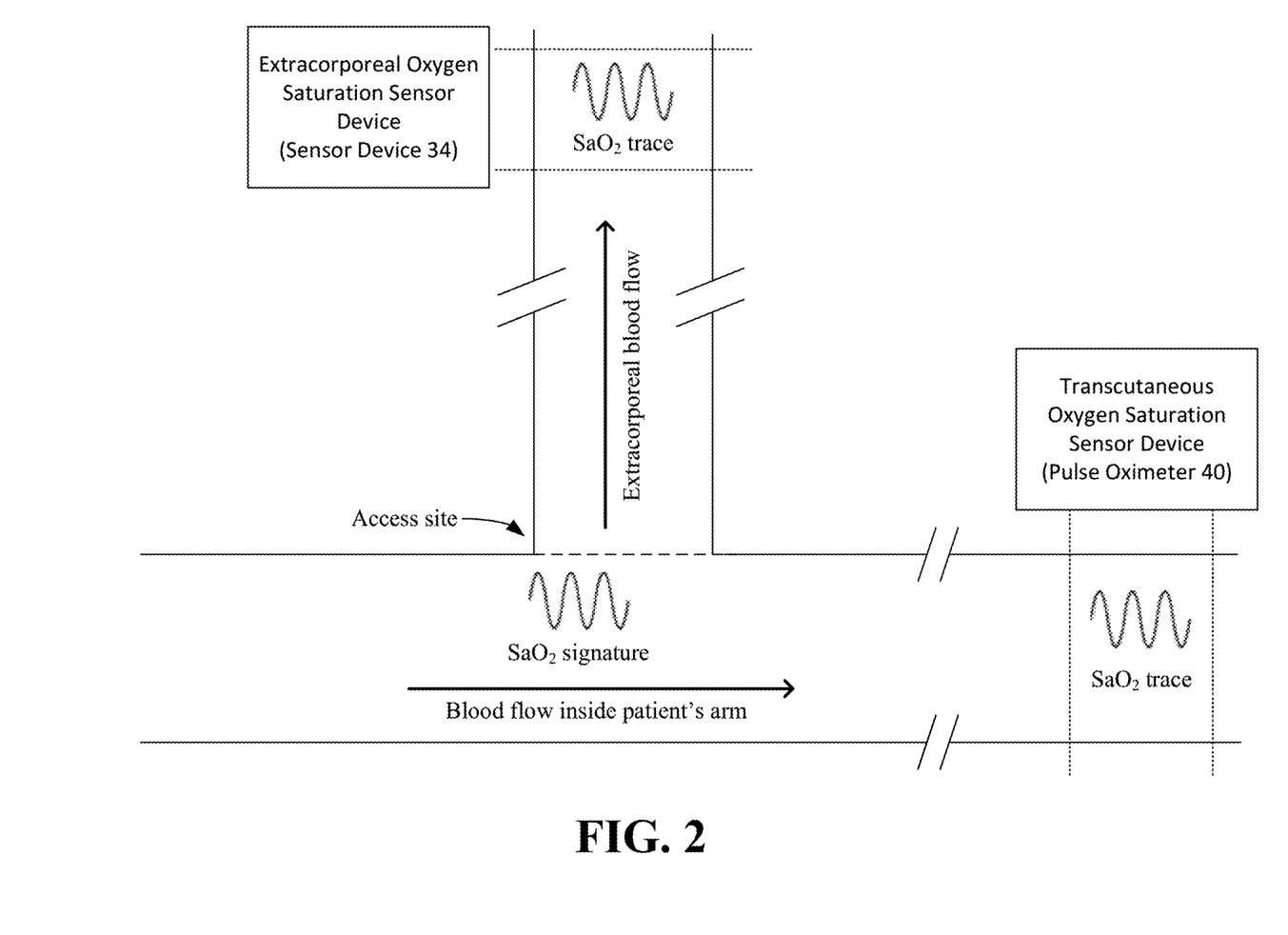
FIG. 2 is a block diagram illustrating an extracorporeal oxygen saturation sensor device disposed in an extracorporeal blood flow path and a transcutaneous oxygen saturation sensor device disposed on a patient's body taking oxygen saturation ($SaO_2$) measurements corresponding to an $SaO_2$ signature of the patient.

FIG. 2 is a block diagram illustrating an extracorporeal oxygen saturation sensor device disposed in an extracorporeal blood flow path and a transcutaneous oxygen saturation sensor device disposed on a patient's body taking oxygen saturation ($SaO_2$) measurements corresponding to an $SaO_2$ signature of the patient.

As blood flows within the patient, for example, through the patient's arm, the blood carries an $SaO_2$ signature corresponding to variations in oxygen saturation levels in the patient's blood. The variations may correspond to breathing patterns of the patient. For example, the $SaO_2$ signature may include peaks corresponding to parts of the patient's blood that has relatively high oxygen saturation values and valleys corresponding to parts of the patient's blood that has relatively low oxygen saturation values.

For a patient undergoing hemodialysis, at the access site, the blood flow along an artery in the patient's arm is split into two different paths. One path corresponds to the arteriovenous access and the extracorporeal blood flow in an extracorporeal blood circuit, wherein an extracorporeal oxygen saturation sensor device (e.g., sensor device 34 as depicted in FIG. 1) is disposed along the extracorporeal blood flow path. The other path corresponds to the blood flow within the patient's arm continuing along the patient's artery (past the access site (e.g., an anastomosis with an arteriovenous access)) and dependent capillary bed wherein a transcutaneous oxygen saturation sensor device (e.g., pulse oximeter 40 as depicted in FIG. 1) is disposed on the patient's body at a location distal to the access site (e.g., attached to a finger).

Both the extracorporeal blood flow path and the blood flow path within the patient's arm carry the $SaO_2$ signature of the patient's blood. However, the travel time from the access site to the position of the extracorporeal oxygen saturation sensor device ($TT_{extracorporeal}$) is independent from the travel time from the access site to the position of the transcutaneous oxygen saturation sensor device ($TT_{transcutaneous}$) due to differences in the flow paths and flow rates and the fact that the extracorporeal flow rate is independent of cardiac output. Thus, for a respective point or segment of the $SaO_2$ signature, the corresponding oxygen saturation measurements taken by the extracorporeal oxygen saturation sensor device will typically be offset in time from the corresponding oxygen saturation measurements taken by the transcutaneous oxygen saturation sensor device (in certain situations, the offset may be zero or close to zero by coincidence). This offset is referred to in the present application as an oxygen signature phase shift (OSPS).

It will be appreciated that travel time from the access site as discussed herein with respect to an AVF access site corresponds to travel time from the location of an arteriovenous anastomosis and with respect to AVG corresponds to travel time from the location where an AV graft is attached to an artery.

In an exemplary embodiment, the oxygen saturation measurements taken by the extracorporeal oxygen saturation sensor device and the oxygen saturation measurements taken by the transcutaneous oxygen saturation sensor device form respective $SaO_2$ traces. The respective $SaO_2$ traces detected at the extracorporeal oxygen saturation sensor device and the transcutaneous oxygen saturation sensor device should include a sufficient amount of data for comparing the traces to one another to determine the OSPS between the traces. For example, a sampling rate of 1 Hz or faster (i.e., at least 1 data point per second) may be used for both sensor devices, with data being gathered over a period of time, for example, of 5 minutes or longer. In other exemplary embodiments, other sampling rates and time periods may be used. For example, a sampling rate of 0.2 Hz or faster (i.e., at least 1 data point every 5 seconds) may be used.

Figure 3:
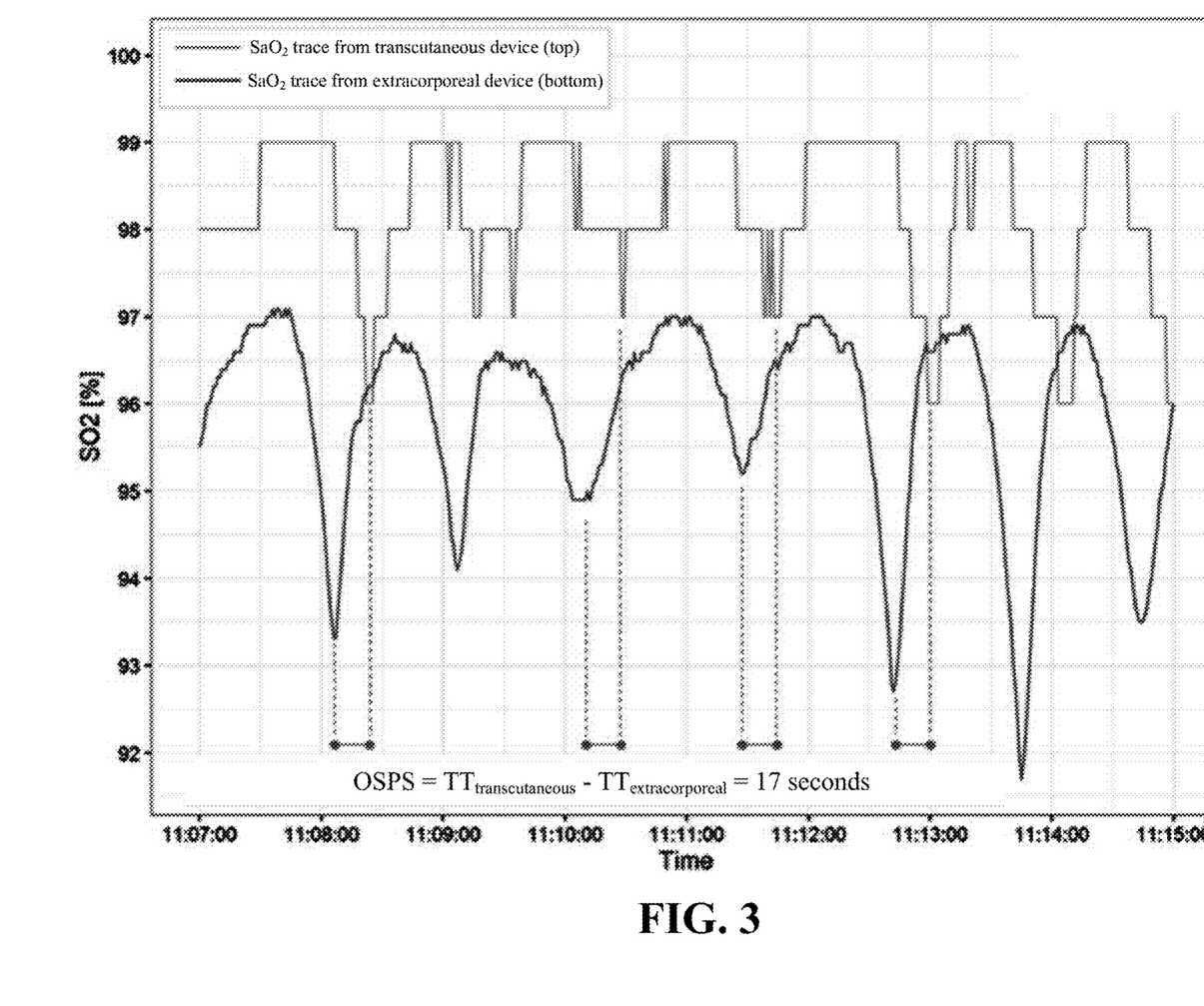
FIG. 3 is a plot illustrating an oxygen signature phase shift (OSPS) between a first $SaO_2$ trace as measured by a transcutaneous oxygen saturation sensor device and a second $SaO_2$ trace as measured by an extracorporeal oxygen saturation sensor device.

FIG. 3 is a plot illustrating an exemplary OSPS between a first $SaO_2$ trace detected by a transcutaneous oxygen saturation sensor device and a second $SaO_2$ trace detected by an extracorporeal oxygen saturation sensor device. In this example, based on certain valleys in the two $SaO_2$ traces which were determined as corresponding to each other, an OSPS (corresponding to the difference between $TT_{transcutaneous}$ and $TT_{extracorporeal}$) of 17 seconds was determined. It will be appreciated that, in the example depicted in FIG. 3, the sensitivity of the transcutaneous oxygen saturation sensor device (increments of 1 percentage point) is relatively lower than the sensitivity of the extracorporeal oxygen saturation sensor device (increments of 0.1 percentage points). In other exemplary embodiments, both devices may have sensitivities which provide oxygen saturation measurements in increments of 0.1 percentage points (or with higher sensitivity) for improved accuracy.

It will be appreciated that the respective $SaO_2$ traces detected by the extracorporeal oxygen saturation sensor device and the transcutaneous oxygen saturation sensor device may be different from one another, as can be seen in FIG. 3. These differences may be due to differences in the equipment used for the respective measurements, as well as due to changes in the oxygen saturation levels in the blood as it travels along the respective flow paths between the access site and the extracorporeal oxygen saturation sensor device and between the access site and the transcutaneous oxygen saturation sensor device (which may cause the $SaO_2$ signatures of the blood at each of the detection sites to be slightly different relative to the (undetected) $SaO_2$ signature in the arterial blood of the patient). However, these differences do not prevent an OSPS from being determined, as the overall shape of the detected $SaO_2$ traces may still be correlated to one another to determine the difference between arrival times at the different detection sites.

If a particular feature of the $SaO_2$ signature of the arterial blood is detected at the extracorporeal oxygen saturation sensor device at time $t_{extracorporeal}$, and that same particular feature of the $SaO_2$ signature of the arterial blood is correspondingly detected at the transcutaneous oxygen saturation sensor device at time $t_{transcutaneous}$, the OSPS can be determined based on the difference between $t_{transcutaneous}$ and $t_{extracorporeal}$. $t_{transcutaneous}$ and $t_{extracorporeal}$ may be determined based on respective clocks of the extracorporeal oxygen saturation sensor device and the transcutaneous oxygen saturation sensor device, which may be synchronized.

Further, a difference between $t_{transcutaneous}$ and $t_{extracorporeal}$ corresponds to the difference between $TT_{transcutaneous}$ and $TT_{extracorporeal}$, and $TT_{extracorporeal}$ can be determined based on the blood flow rate through the extracorporeal blood line and the volume of the portion of the extracorporeal blood line between the arterial cannula and the position of the extracorporeal oxygen saturation sensor device (i.e., $TT_{extracorporeal}$ [min]=volume of relevant portion of blood line [mL]/blood flow rate [mL/min]). This means that $TT_{transcutaneous}$ can be determined based on $t_{transcutaneous}$, $t_{extracorporeal}$, and $TT_{extracorporeal}$ (e.g., $TT_{transcutaneous} = t_{transcutaneous} - t_{extracorporeal} + TT_{extracorporeal}$). For example, if the blood flow rate in the extracorporeal blood line is 400 mL/min and the volume of the relevant portion of the extracorporeal blood line is 100 mL, $TT_{extracorporeal}$ is 0.25 minutes (i.e., 15 seconds). Further, if $t_{transcutaneous} - t_{extracorporeal}$ is 17 seconds (e.g., corresponding to the OSPS depicted in FIG. 3), $TT_{transcutaneous}$ is determined as being 32 seconds (17 seconds+15 seconds). It will be appreciated that the determined difference may be an approximation or an estimation of an actual difference, as the effective extracorporeal blood flow rate may not always be exactly the same as the one that is dialed into a blood pump.

It will be appreciated that, depending on a variety of factors (e.g., extracorporeal blood volume between the arterial cannula and the position of the extracorporeal oxygen saturation sensor device, vascular access flow rate, arterial volume between the access site and the position of the transcutaneous oxygen saturation sensor device, blood flow rate through the extracorporeal blood line, the patient's cardiac output, arteriolar tone, etc.), $TT_{transcutaneous}$ may be longer than, the same as, or shorter than $TT_{extracorporeal}$.

It will be appreciated that FIG. 2 provides a simplified depiction of the described blood flow paths. For example, in the case of AVF/AVG, there may be a short blood flow segment between an AVF/AVG anastomosis and an arterial cannulation site, which would mean that $TT_{extracorporeal}$ may actually correspond to the volume of the relevant portion of blood line [mL] divided the blood flow rate [mL/min], plus an AVF/AVG transit time. However, this AVF/AVG transit time can be neglected because it is negligible in magnitude (i.e., its impact on the OSPS value would not represent a meaningful difference with respect to the patient's cardiac output or hemodynamic status).

In the example depicted in FIG. 1, the transcutaneous oxygen saturation sensor device (pulse oximeter 40) is disposed on a fingertip of the patient on the same arm on which the access site is disposed. In other exemplary embodiments, the transcutaneous oxygen saturation sensor device may be disposed at other locations on the patient's body, and other types of transcutaneous oxygen saturation sensor devices may be used (e.g., transcutaneous oxygen saturation sensor devices which are attachable to a patient's earlobe, forehead, toe, wrist, nose, lip, cheek, or other body part). It may be advantageous to position the transcutaneous oxygen saturation sensor device at a location that is ipsilateral to the access site to more easily correlate the oxygen saturation measurements taken by the transcutaneous oxygen saturation sensor device and the extracorporeal oxygen saturation sensor device.

Figure 4A:
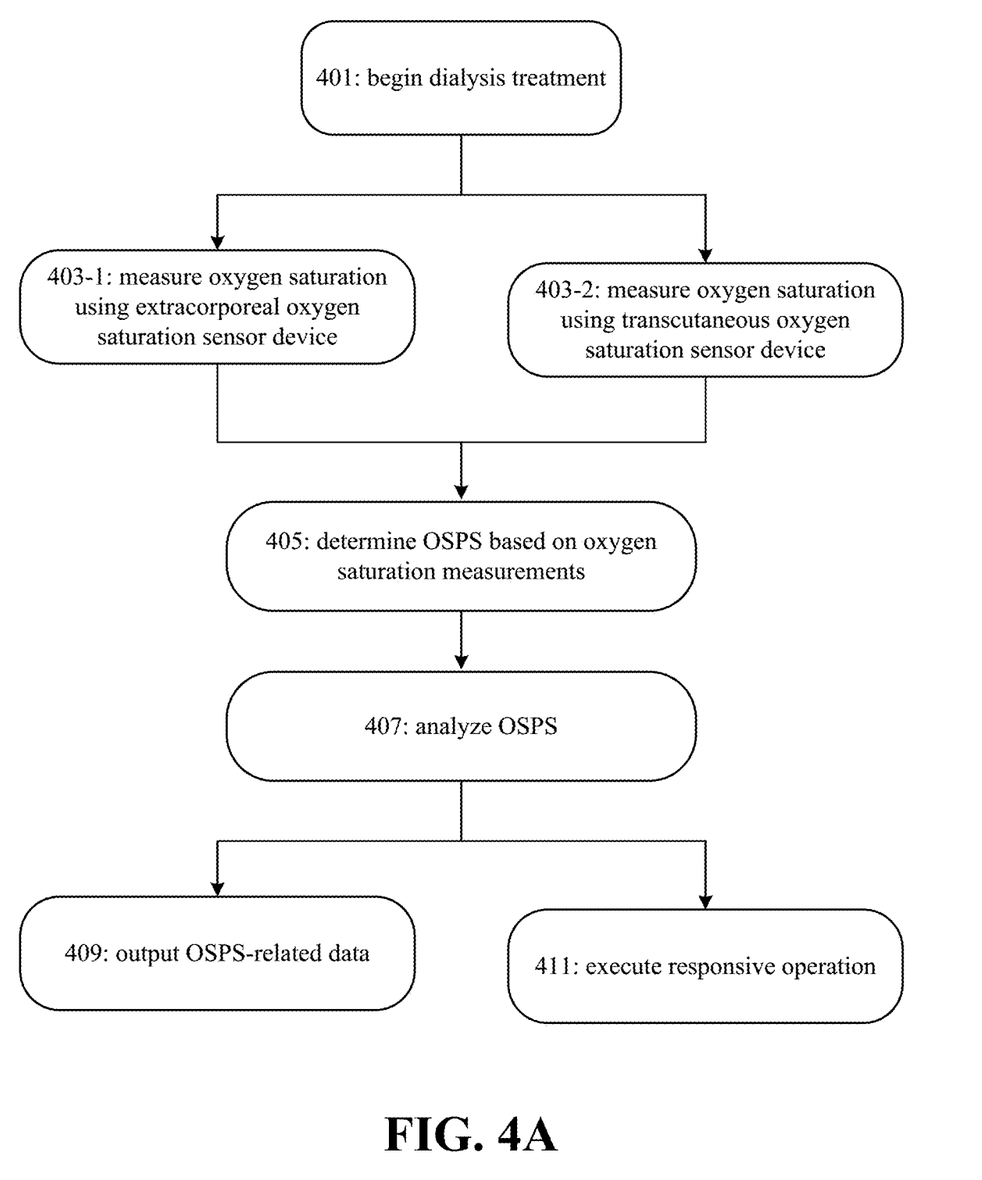
FIG. 4A is a flowchart of an exemplary process for intradialytic monitoring of a patient's OSPS.

FIG. 4 is a flowchart of an exemplary process for intradialytic monitoring of a patient's OSPS. At stage 401, a dialysis treatment for a patient begins, for example, based on operation of a hemodialysis system to which the patient is connected, wherein the hemodialysis system has an extracorporeal oxygen saturation sensor device and a transcutaneous oxygen saturation sensor device (for example, as discussed above in connection with FIGS. 1-3). At stages 403-1 and 403-2, the extracorporeal oxygen saturation sensor device and the transcutaneous oxygen saturation sensor device obtain oxygen saturation measurements at respective detection sites (for example, as discussed above in connection with FIGS. 1-3).

At stage 405, one or more OSPS values are determined for the patient based on the oxygen saturation measurements. In an exemplary embodiment, a respective OSPS value for the patient may correspond to a sampling window, wherein respective $SaO_2$ traces detected by the extracorporeal oxygen saturation sensor device and the transcutaneous oxygen saturation sensor device during the sampling window are compared to one another. In the example depicted in FIG. 3, the sampling window is 8 minutes, but it will be appreciated that other sampling window sizes (e.g., within the range of 5-10 minutes) may be used in other exemplary embodiments.

The sampling window may, for example, be a rolling window such that a new OSPS value is determined repeatedly each time the sampling window moves forward in time by an increment. The increment may be as small as the sampling rate provided by the extracorporeal oxygen saturation sensor device or the transcutaneous oxygen saturation sensor device. For example, if the sampling rate provided by at least one of the sensor devices is 1 Hz, new OSPS values may be determined every second as new oxygen saturation measurements are obtained. In another example, a new OSPS value may be determined at longer increments that are larger than the sampling rates provided by the sensor devices. In yet another example, instead of using a rolling window, non-overlapping sampling windows may be used (e.g., given a sampling window of 8 minutes, a new OSPS value would be periodically determined at most once every 8 minutes).

An average OSPS may be calculated per sampling window. For example, in FIG. 3, a monitoring device has multiple opportunities to determine individual OSPS values, and all of those individual OSPS values can then be averaged over the sampling window to obtain a more reliable point estimate for the window. The window size may be selected to be wide enough to allow a) reliable identification of which points in one trace correspond to which points in the other trace and b) identification of multiple OSPS values that can then be averaged. After that, the sampling/analysis window can be shifted forward by an amount that corresponds to a clinically useful update frequency for hemodynamic monitoring (e.g., 3 minutes or 5 minutes). Some overlap with the previous sampling/analysis window may be beneficial, as corresponding points between the two curves are already known for the overlapping segment of the window, and can be used as a reference for new portions of a current window.

The determination of the OSPS from the respective $SaO_2$ traces within a sampling window may be based on a cross-correlation analysis using the respective $SaO_2$ traces and/or a pattern recognition analysis using the respective $SaO_2$ traces.

The determination at stage 405 may be made by a controller (such as the controller of display device 35 of FIG. 1) that is in communication with both sensor devices.

At stage 407, one or more OSPS values as determined at stage 405 may be analyzed. The analysis may be performed, for example, on a rolling basis as new OSPS values are determined.

One aspect of the analysis at stage 407 may include determining a trend in OSPS values (trend analysis). For example, if the OSPS values for the patient are increasing over time, this may indicate a problem with the patient's perfusion (e.g., due to decreased cardiac output or increased peripheral resistance). Thus, if a current OSPS value determined for the patient is lower than a previous OSPS value (e.g., an immediately previous OSPS value, an initial OSPS value at the start of the treatment, or a previous highest OSPS value) by more than a threshold amount, a potential problem associated with the patient's hemodynamic status is detected. In another example, the OSPS values that are used in the analysis may be average values (e.g., the trend analysis may include comparing the average of the last three OSPS values with the average of the previous three OSPS values before the last three OSPS values). In other exemplary embodiments, other types of trend analysis may be performed to detect a potential problem associated with the patient's hemodynamic status.

In a further exemplary embodiment, an analysis of a derivative of the OSPS values may be performed. For example, a derivative of the OSPS values may be utilized to detect whether a change in OSPS values is accelerating over time.

Although less common, the OSPS values for the patient decreasing over time may also be indicative of a problem (e.g., increasing stiffness of vasculature). Thus, a potential problem associated with the patient's hemodynamic status may also be detected based on a downwards trend in the OSPS values for the patient.

Another aspect of the analysis at stage 407 may include comparison of a current OSPS value of the patient (or an average OSPS value of the patient based on multiple determined OSPS values for the patient) to one or more reference OSPS values (reference-based analysis). The one or more reference OSPS values may include an upper limit value or a lower limit value. Further, the one or more reference OSPS values may be based on one or more demographic categories applicable to the patient (e.g., gender, age range, ethnicity, etc.), based on physical characteristics of the patient (e.g., height or weight), based on placement location of the transcutaneous oxygen saturation sensor device (e.g., ipsilateral hand, contralateral hand, earlobe, etc.), and/or based on previous OSPS values for the patient. When it is determined that an OSPS value of the patient is above an upper limit value or is below a lower limit value, a potential problem associated with the patient's hemodynamic status is detected. For example, if the patient's OSPS value is unusually high or unusually low, there may be a problem with the patient's perfusion (such as low cardiac output or high peripheral resistance corresponding to high OSPS, or stiff vasculature corresponding to low OSPS).

It will be appreciated that, even within a particular demographic or a particular set of demographics, there may be significant hemodynamic-related variations from patient-to-patient, so the upper and lower limit values may be set to be relatively high and relatively low, respectively, to avoid false alarms with respect to detecting potential problems associated with the patient's hemodynamic status.

The analysis at stage 407 may alternatively be performed based on $TT_{transcutaneous}$ instead of based on OSPS. For example, stage 407 may include determination of $TT_{transcutaneous}$ value(s) corresponding to OSPS value(s), and using the determined $TT_{transcutaneous}$ value(s) to perform a trend analysis (e.g., determining whether $TT_{transcutaneous}$ is increasing or decreasing over time) or a reference-based analysis (e.g., determining whether $TT_{transcutaneous}$ is higher than an upper limit value or lower than a lower limit value) in a similar manner as discussed above with respect to using OSPS value(s) to perform the trend analysis or the reference-based analysis.

The analysis at stage 407 may be performed by the controller that is in communication with both sensor devices or by another controller (e.g., a controller of a remote monitoring device).

At stage 409, OSPS-related data may be output. The OSPS-related data may include, for example, the one or more OSPS values determined at stage 405, one or more $TT_{transcutaneous}$ values, and/or results of one or more analyses performed at stage 407. Outputting the OSPS-related data may include displaying the one or more OSPS values determined at stage 405, one or more $TT_{transcutaneous}$ values, and/or results of one or more analyses performed at stage 407 on a display, such as on a display of the display device 35 of FIG. 1 and/or a display of a remote monitoring device. Outputting the OSPS-related data may also include sending the one or more OSPS values determined at stage 405, one or more $TT_{transcutaneous}$ values, and/or results of one or more analyses performed at stage 407 over a network to a medical professional and/or to an electronic health records (EHR) system.

At stage 411, a responsive operation may be executed based on results of one or more analyses performed at stage 407. For example, if a trend analysis performed at stage 407 indicates that the patient's OSPS or $TT_{transcutaneous}$ values are trending upwards or downwards, or if a reference-based analysis performed at stage 407 indicates that the patient's OSPS or $TT_{transcutaneous}$ value is unusually high or unusually low, one or more of the following responsive operations (e.g., for increasing hemodynamic stability) may be executed by a controller (such as a controller of the hemodialysis machine 12 depicted in FIG. 1, a controller of display device 35 depicted in FIG. 1, or a controller of a remote monitoring device):

Lowering an ultrafiltration rate for the dialysis treatment being performed for the patient. This may include utilizing the results of the analysis at stage 407 as one input of multiple inputs into an algorithm for determining the ultrafiltration rate for the dialysis treatment.

Pausing the dialysis treatment.

Adjusting the patient position (e.g., via communication with an electronically-adjustable bed or chair), for example, by changing the patient from a sitting position to a supine position and/or by raising the patient's legs and/or by placing the patient in the "Trendelenburg position" (supine with lowered upper body and raised legs) to cause blood in the lower extremities to shift towards the central circulation (known as "autotransfusion").

Controlling operation of a heater to lower dialysate temperature.

Controlling operation of a saline pump to infuse saline.

Controlling a dialysate mixing process to increase sodium concentration in the dialysate.

Triggering more frequent measurements of blood pressure to provide closer monitoring of the patient's hemodynamic status.

Triggering an alarm and/or a notification to alert a medical professional to provide a treatment intervention.

Each of the foregoing interventions identified above may be performed automatically. Alternatively, an alarm and/or notification may include an instruction to the medical professional to perform one or more of the foregoing interventions in this list.

By providing for treatment interventions in a timely manner at stage 409 based on real-time analysis at stage 407, exemplary embodiments of the present application are able to avert, reverse, or mitigate problematic hemodynamic changes in a patient, which may have otherwise caused serious (and possibly life-threatening) problems such as blood pressure drops and organ hypoperfusion. Avoidance of such intradialytic complications also leads to lower long-term mortality risk.

A patient's $SaO_2$ signature, which contains peaks and valleys in oxygen saturation levels, may be based on his or her breathing pattern. In certain exemplary embodiments, it may be advantageous to induce a clearer $SaO_2$ signature in a patient by providing the patient with supplemental oxygen, thereby triggering one or more artificially-induced increases in oxygen saturation levels corresponding to the provision of the supplemental oxygen. These artificially-induced increases may help to make the OSPS determination at stage 405 more accurate and reliable.

Figure 4B:
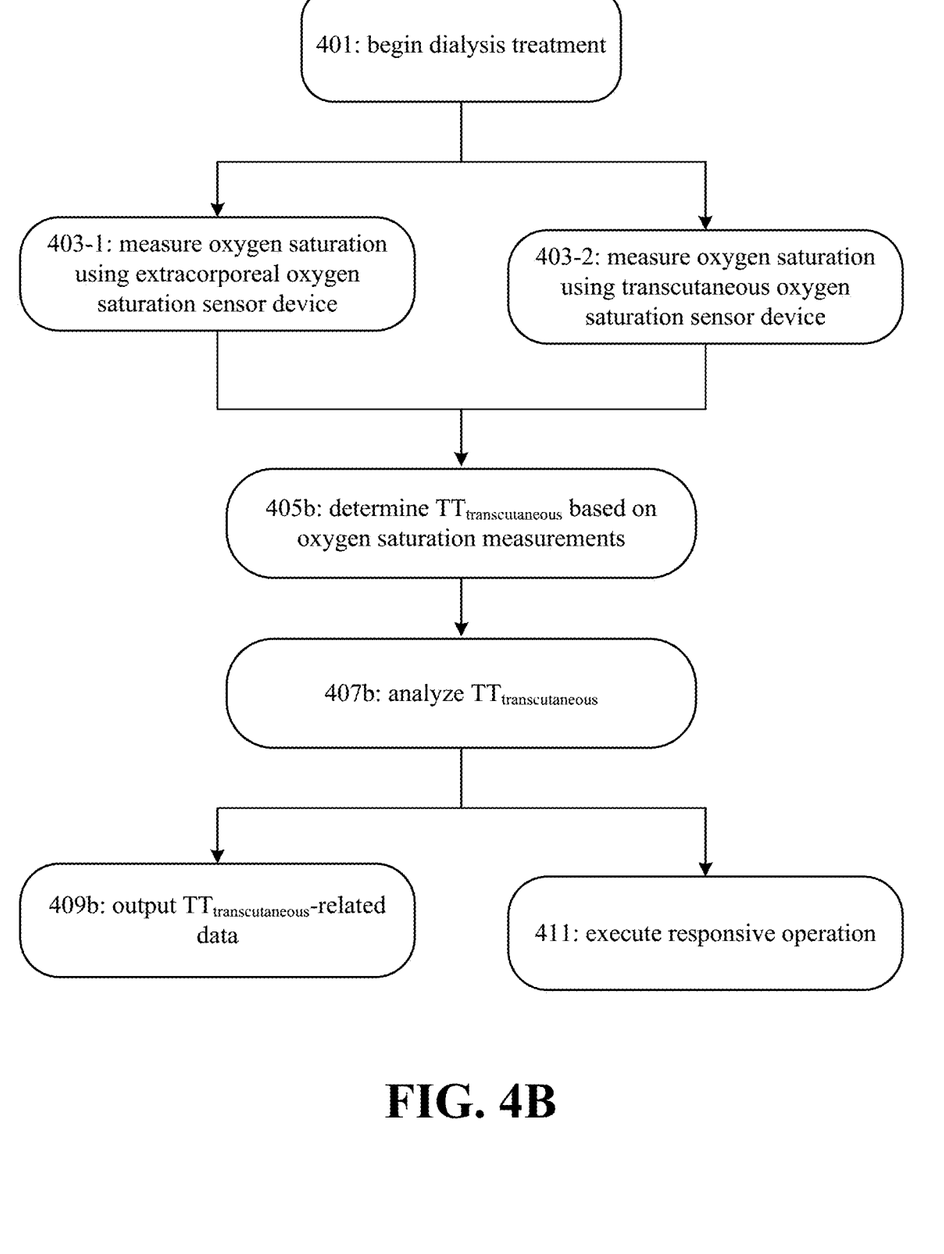
FIG. 4B is a flowchart of an exemplary process for intradialytic monitoring of a transcutaneous travel time of a patient.

FIG. 4B is a flowchart of an exemplary process for intradialytic monitoring of a transcutaneous travel time of a patient. FIG. 4B is similar to FIG. 4A, but instead of stages 405, 407 and 409 being performed, stages 405b, 407b and 409b are performed. At stage 405b, one or more $TT_{transcutaneous}$ values for the patient are determined. At stage 407b, an analysis of $TT_{transcutaneous}$ value(s) is performed (for example, in accordance with the discussion above with regard to analyzing $TT_{transcutaneous}$ value(s) in the context of stage 407). Stage 407b may also include a determination of OSPS value(s) based on the $TT_{transcutaneous}$ value(s) and an analysis thereof (for example, in accordance with the discussion above with regard to analyzing OSPS value(s) in the context of stage 407). At stage 409b, $TT_{transcutaneous}$-related data (which may be similar to the OSPS-related data as discussed above in the context of stage 409) is output. It will be appreciated that exemplary embodiments corresponding to FIG. 4B may be advantageous, for example, in situations where the extracorporeal flowrate is changed during the course of ongoing measurements, which could complicate the determination of OSPS (due to the OSPS determined from the offset between the two timeseries changing, in which case new OSPS values would need to be corrected to make them comparable to the OSPS values prior to the change in extracorporeal flowrate) but does not affect the determination of $TT_{transcutaneous}$ (since $TT_{transcutaneous}$ is determined based on $TT_{extracorporeal}$, which is what changes in response to a change in extracorporeal flowrate).

Figure 5:
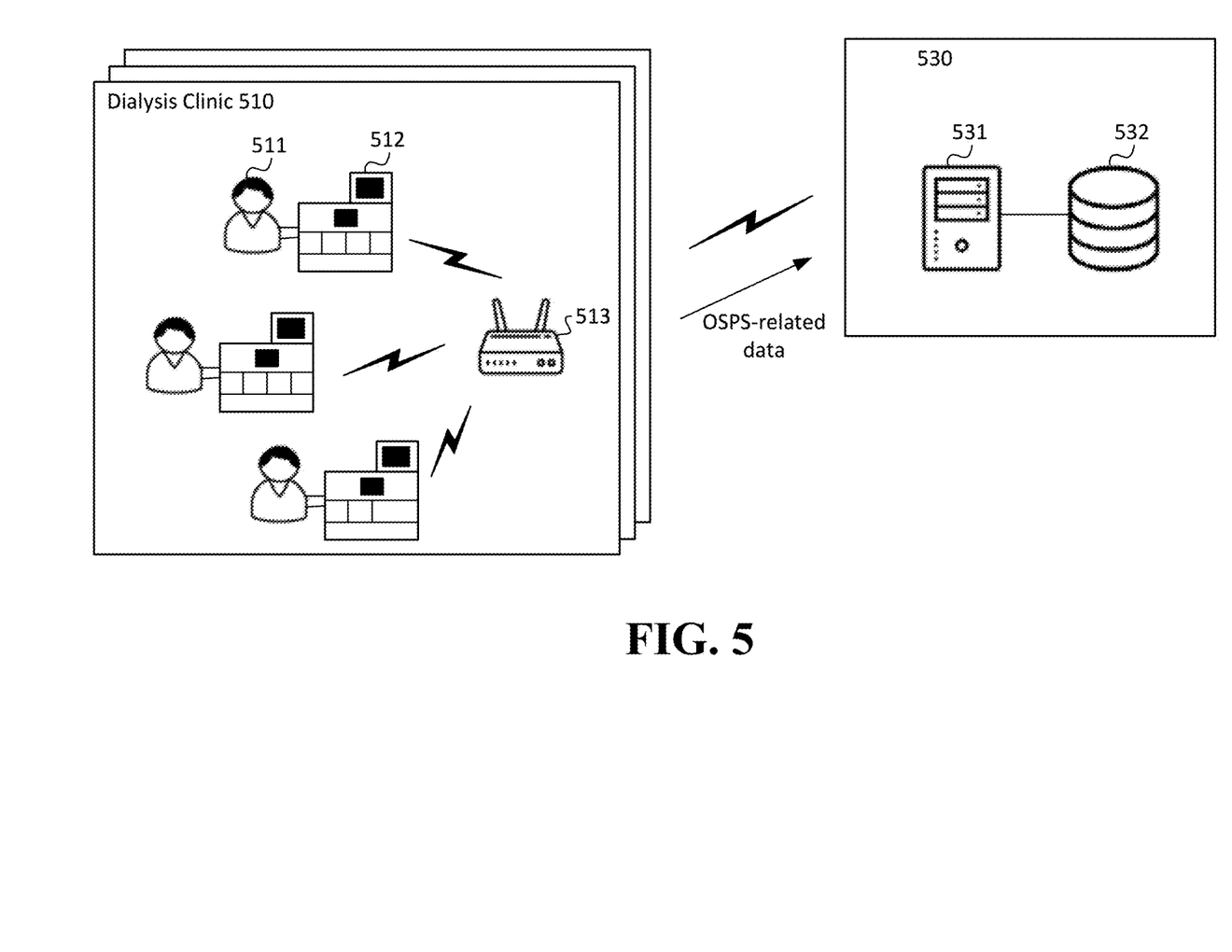
FIG. 5 is a block diagram of an exemplary network environment in which a hemodialysis system communicates with an electronic health records (EHR) system to provide OSPS-related or $TT_{transcutaneous}$-related data to the EHR system.

FIG. 5 is a block diagram of an exemplary network environment in which a hemodialysis system communicates with an electronic health records (EHR) system to provide OSPS-related or $TT_{transcutaneous}$-related data to the EHR system, the OSPS-related or $TT_{transcutaneous}$-related data including, for example, one or more OSPS values determined in accordance with stage 405 discussed above, one or more $TT_{transcutaneous}$ values, and/or results of one or more analyses performed in accordance with stage 407 discussed above. The network environment includes one or more dialysis clinics (including a respective dialysis clinic 510) and an EHR system 530.

The dialysis clinic 510 includes one or more hemodialysis systems used to provide hemodialysis treatment to one or more patients (including a respective patient 511 and a respective hemodialysis system 512). Each of the hemodialysis systems is in communication with a gateway device 513, for example, via a wired connection (e.g., an Ethernet RJ-45 connection or a fiber optic connection) or a wireless connection (e.g., via Bluetooth or WiFi). For example, a display device or a sensor device of an optical blood monitoring system of each of the hemodialysis systems may include a communications interface and corresponding communications equipment for communicating with the gateway device via the wired or wireless connection. The gateway device 513 is configured to communicate with an EHR system 530 over one or more networks (such as via a private computing network, via a public computing network such as the Internet, and/or via a mobile communications network). The EHR system 530 includes, for example, at least one application server 531 and at least one database 532 connected to the at least one application server 531. The EHR system 330 is configured, among other things, to store patient health information (e.g., pertaining to patient 511 and other patients being treated at the one or more dialysis clinics) in the at least one database 532 and to process and respond to requests for electronic health information via the at least one application server 531. The EHR system 530 receives patient health information from various sources, including the one or more dialysis clinics, and the EHR system 530 may be configured to communicate with the various sources over one or more networks (such as via a private computing network, via a public computing network such as the Internet, and/or via a mobile communications network).

In accordance with exemplary embodiments of the present application, as shown in FIG. 5, the dialysis clinic 510 may further provide OSPS-related or $TT_{transcutaneous}$-related data corresponding to patient 511 to the EHR system 530 for storage and/or for further analysis or processing. The OSPS-related or $TT_{transcutaneous}$-related data may be sent to the EHR system 530 in real-time or in batches, and the EHR system 530 may maintain historical OSPS-related or $TT_{transcutaneous}$-related data for a plurality of patients in the at least one database 532. Further, based on the historical OSPS-related or $TT_{transcutaneous}$-related data for a particular patient, the EHR system (or another system in communication with the EHR system) may detect a potential chronic issue for the patient that evolves relatively slowly (e.g., over the course of multiple treatments or several months or even years), such as increased stiffness of vasculature corresponding to a slow downward trend in OSPS or $TT_{transcutaneous}$ values for the patient across multiple treatments.

The EHR system 530 (or another system in communication with the dialysis clinic 510) may be configured for remote monitoring of dialysis treatments being performed at the dialysis clinic 510, such that responsive actions based on the OSPS-related or $TT_{transcutaneous}$-related data or based on analysis of the OSPS-related or $TT_{transcutaneous}$-related data may be triggered remotely. Further, the EHR system 530 (or another system in communication with the EHR system) may utilize aggregated OSPS-related or $TT_{transcutaneous}$-related data from a plurality of patients to determine one or more OSPS or $TT_{transcutaneous}$ reference values, wherein the one or more OSPS or $TT_{transcutaneous}$ reference values may, for example, correspond to one or more demographic categories. The EHR system 530 (or another system in communication with the EHR system) may also determine one or more OSPS or $TT_{transcutaneous}$ reference values for an individual patient based on the patient's history of OSPS or $TT_{transcutaneous}$ values and/or the patient's history of intradialytic complications. The determined OSPS or $TT_{transcutaneous}$ reference values may be optimal reference values (which provide a favorable sensitivity/specificity tradeoff). Further, the determined OSPS or $TT_{transcutaneous}$ reference value(s) may be sent over the network to whichever controller is performing analysis on determined OSPS or $TT_{transcutaneous}$ values.

It will be appreciated that the network environment depicted in FIG. 5 is merely exemplary, and that the principles discussed herein are also applicable to other types of network configurations, entities, and equipment.

It will be appreciated that although the exemplary embodiments discussed above include a first oxygen saturation sensor device which is an extracorporeal oxygen saturation sensor device and a second oxygen saturation sensor device which is a transcutaneous oxygen saturation sensor device (e.g., a pulse oximeter), the present application is not limited thereto. For example, for the second oxygen saturation sensor device, other types of oxygen saturation sensor devices may also be used, such as oxygen saturation sensor devices which utilize an arterial line (e.g., a small catheter inserted into an artery, typically the radial artery near the wrist) to measure arterial blood gases or oxygen saturation sensor devices which utilize camera-based oxygen saturation measurement techniques.

Exemplary embodiments of the present application provide for improved cardiovascular monitoring during dialysis in a nonintrusive, inexpensive and continuous manner. By using oxygen saturation measurements taken by both an extracorporeal oxygen saturation sensor device and a transcutaneous oxygen saturation sensor device, one or more OSPS or $TT_{transcutaneous}$ values for a patient may be determined in real-time, whereby the determined OSPS or $TT_{transcutaneous}$ value(s) are indicative of the patient's hemodynamic status. Thus, based on analysis of the determined OSPS or $TT_{transcutaneous}$ value(s), deteriorations in hemodynamic stability may be detected and responded to in a timely manner, and patient safety and outcomes may be improved.

It will be appreciated that the various machine-implemented operations described herein may occur via the execution, by one or more respective processors, of processor-executable instructions stored on a tangible, non-transitory computer-readable medium, such as a random access memory (RAM), read-only memory (ROM), programmable read-only memory (PROM), and/or another electronic memory mechanism. Thus, for example, operations performed by any device described herein may be carried out according to instructions stored on and/or applications installed on the device, and via software and/or hardware of the device.

All references, including publications, patent applications, and patents, cited herein are hereby incorporated by reference to the same extent as if each reference were individually and specifically indicated to be incorporated by reference and were set forth in its entirety herein.

While the invention has been illustrated and described in detail in the drawings and foregoing description, such illustration and description are to be considered illustrative or exemplary and not restrictive. It will be understood that changes and modifications may be made by those of ordinary skill within the scope of the following claims. In particular, the present application covers further embodiments with any combination of features from different embodiments described above and below.

The terms used in the claims should be construed to have the broadest reasonable interpretation consistent with the foregoing description. For example, the use of the article "a" or "the" in introducing an element should not be interpreted as being exclusive of a plurality of elements. Likewise, the recitation of "or" should be interpreted as being inclusive, such that the recitation of "A or B" is not exclusive of "A and B," unless it is clear from the context or the foregoing description that only one of A and B is intended. Further, the recitation of "at least one of A, B and C" should be interpreted as one or more of a group of elements consisting of A, B and C, and should not be interpreted as requiring at least one of each of the listed elements A, B and C, regardless of whether A, B and C are related as categories or otherwise. Moreover, the recitation of "A, B and/or C" or "at least one of A, B or C" should be interpreted as including any singular entity from the listed elements, e.g., A, any subset from the listed elements, e.g., A and B, or the entire list of elements A, B and C.

Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

The invention claimed is:

1. A hemodialysis system, comprising:
   a hemodialysis machine configured to provide hemodialysis treatment to a patient, wherein the hemodialysis treatment includes circulating extracorporeal blood of the patient through an extracorporeal blood circuit;
   a first oxygen saturation sensor device configured to measure oxygen saturation corresponding to the extracorporeal blood of the patient in the extracorporeal blood circuit;
   a second oxygen saturation sensor device configured to measure oxygen saturation corresponding to blood flowing within the patient; and
   at least one controller configured to determine one or more oxygen saturation phase shift (OSPS) values or one or more transcutaneous travel time values corresponding to the patient based on oxygen saturation measurements from the first oxygen saturation sensor device and the second oxygen saturation sensor device.

2. The hemodialysis system according to claim 1, wherein the extracorporeal blood of the patient is drawn from the patient from an access site, and wherein the second oxygen saturation sensor device is adapted to be located on the patient ipsilateral to the access site.

3. The hemodialysis system according to claim 2, wherein the access site and the second oxygen saturation sensor device are both adapted to be located on a same arm of the patient.

4. The hemodialysis system according to claim 3, wherein the second oxygen saturation sensor device is a pulse oximeter adapted to be attached to a finger of the patient.

5. The hemodialysis system according to claim 1, wherein determining the one or more OSPS values or the one or more transcutaneous travel time values comprises comparing a first oxygen saturation trace corresponding to measurements taken by the first oxygen saturation sensor device with a second oxygen saturation trace corresponding to measurements taken by the second oxygen saturation sensor device.

6. The hemodialysis system according to claim 1, wherein the first oxygen saturation sensor device and the second oxygen saturation sensor device each have a sampling rate of at least 1 Hz.

7. The hemodialysis system according to claim 1, wherein the at least one controller is further configured to analyze the one or more determined OSPS values or the one or more determined transcutaneous travel time values, wherein the analysis includes a trend analysis which identifies an upward or downward trend in determined OSPS values or determined transcutaneous travel time values for the patient.

8. The hemodialysis system according to claim 1, wherein the at least one controller is further configured to analyze the one or more determined OSPS values or the one or more determined transcutaneous travel time values, wherein the analysis includes a reference-based analysis which identifies whether a determined OSPS value or a determined transcutaneous travel time value for the patient is above or below one or more reference OSPS values or one or more reference transcutaneous travel time values.

9. The hemodialysis system according to claim 1, wherein each of the one or more determined transcutaneous travel time values corresponds to a respective amount of time for blood to travel between an access site for drawing the extracorporeal blood and a location of the second oxygen saturation sensor device.

10. The hemodialysis system according to claim 1, wherein the at least one controller is further configured to analyze the one or more determined OSPS values or the one or more determined transcutaneous travel time values, and to output a result of the analysis, wherein outputting the result includes displaying the result on a display and/or transmitting the result over a communication network.

11. The hemodialysis system according to claim 1, wherein the at least one controller is further configured to analyze the one or more determined OSPS values or the one or more determined transcutaneous travel time values, and to execute a responsive operation in response to a result of the analysis, wherein the responsive operation includes modifying the hemodialysis treatment for the patient.

12. The hemodialysis system according to claim 11, wherein the modification includes:
 lowering an ultrafiltration rate;
 pausing the hemodialysis treatment;
 adjusting the patient position;
 lowering dialysate temperature;
 infusing saline;
 increasing sodium concentration in dialysate; and/or
 triggering a relatively higher frequency of blood pressure measurements.

13. The hemodialysis system according to claim 1, wherein the at least one controller is further configured to analyze the one or more determined OSPS values or the one or more determined transcutaneous travel time values, and to execute a responsive operation in response to a result of the analysis, wherein the responsive operation includes outputting an alarm and/or transmitting a message to a medical professional.

14. A method for monitoring hemodynamic status of a patient during a treatment, comprising:
 measuring, by a first oxygen saturation sensor device, oxygen saturation of extracorporeal blood of the patient at a location in an extracorporeal blood circuit;
 measuring, by a second oxygen saturation sensor device, oxygen saturation of blood within the patient at a location on the patient's body;
 determining, by at least one controller, one or more oxygen saturation phase shift (OSPS) values or one or more transcutaneous travel time values corresponding to the patient based on oxygen saturation measurements from the first oxygen saturation sensor device and the second oxygen saturation sensor device;
 analyzing, by the at least one controller, the one or more determined OSPS values or the one or more determined transcutaneous travel time values; and
 executing, by the at least one controller, a responsive operation in response to a result of the analysis.

15. The method according to claim 14, wherein the extracorporeal blood of the patient is drawn from the patient from an access site, and wherein the second oxygen saturation sensor device is located on the patient's body ipsilateral to the access site.

16. The method according to claim 15, wherein the one or more determined transcutaneous travel time values each correspond to an amount of time for blood to travel between the access site and the location of the second oxygen saturation sensor device.

17. The method according to claim 14, wherein the responsive operation includes modifying the treatment.

18. A non-transitory computer-readable medium having processor-executable instructions stored thereon for monitoring hemodynamic status of a patient during a treatment, wherein the processor-executable instructions, when executed, facilitate:
 obtaining, from a first oxygen saturation sensor device, oxygen saturation measurements of extracorporeal blood of the patient at a location in an extracorporeal blood circuit;
 obtaining, from a second oxygen saturation sensor device, oxygen saturation measurements of blood within the patient at a location on the patient's body;
 determining, by at least one controller, one or more oxygen saturation phase shift (OSPS) values or one or more transcutaneous travel time values corresponding to the patient based on the oxygen saturation measurements from the first oxygen saturation sensor device and the second oxygen saturation sensor device;
 analyzing, by the at least one controller, the one or more determined OSPS values or the one or more determined transcutaneous travel time values; and
 executing, by the at least one controller, a responsive operation in response to a result of the analysis.

19. The non-transitory computer-readable medium according to claim 18, wherein the extracorporeal blood of the patient is drawn from the patient from an access site, and wherein the second oxygen saturation sensor device is adapted to be located on the patient's body ipsilateral to the access site.

20. The non-transitory computer-readable medium according to claim 19, wherein each of the one or more determined transcutaneous travel time values corresponds to a respective amount of time for blood to travel between the access site and the location of the second oxygen saturation sensor device.

21. The non-transitory computer-readable medium according to claim 18, wherein the responsive operation includes modifying the treatment.

* * * * *